(12) United States Patent
Liebau et al.

(10) Patent No.: US 11,096,675 B2
(45) Date of Patent: Aug. 24, 2021

(54) SYSTEM FOR THE ASSERVATION OF HAIR SAMPLES

(71) Applicant: Eberhard Karls Universitaet Tuebingen Medizinische Fakultaet, Tuebingen (DE)

(72) Inventors: Stefan Liebau, Rangendingen (DE); Kevin Achberger, Tuebingen (DE)

(73) Assignee: Eberhard Karfs Universitaet Tuebingen Medizinische Fakultaet, Tuebingen (DE)

( * ) Notice: Subject to any disclaimer, the term of this patent is extended or adjusted under 35 U.S.C. 154(b) by 167 days.

(21) Appl. No.: 16/375,125

(22) Filed: Apr. 4, 2019

(65) Prior Publication Data
US 2019/0223847 A1  Jul. 25, 2019

Related U.S. Application Data

(63) Continuation of application No. PCT/EP2017/075336, filed on Oct. 5, 2017.

(30) Foreign Application Priority Data

Oct. 6, 2016  (DE) .................... 10 2016 118 968.5

(51) Int. Cl.
*A61B 10/00*  (2006.01)
*B01L 3/00*  (2006.01)

(52) U.S. Cl.
CPC .......... *A61B 10/0096* (2013.01); *B01L 3/508* (2013.01); *B01L 3/5085* (2013.01); *B01L 2200/025* (2013.01); *B01L 2300/041* (2013.01)

(58) Field of Classification Search
CPC ... A61B 10/0096; B01L 3/508; B01L 3/5085; B01L 2200/025; B01L 2300/041
See application file for complete search history.

(56) References Cited

U.S. PATENT DOCUMENTS 1,801,751 A * 4/1931 Mills .................... A45D 44/005
206/486
5,484,731 A * 1/1996 Stevens ................. B01L 3/5085
206/558

(Continued)

FOREIGN PATENT DOCUMENTS

EP   1 177 769 A2   2/2002
EP   2 284 538 A1   2/2011

(Continued)

OTHER PUBLICATIONS

English-language translation of International Search Report and Written Opinion for International Application No. PCT/EP2017/075336, dated Dec. 21, 2017 (6 pages).

(Continued)

*Primary Examiner* — Jill A Warden
*Assistant Examiner* — Henry H Nguyen
(74) *Attorney, Agent, or Firm* — Klarquist Sparkman, LLP (57) ABSTRACT

A system for asservation of at least one hair including a hair root and a hair shaft are disclosed. In some embodiments, the system includes transport and/or storage containers, or cultivation containers. Also disclosed are methods for transporting and/or storing hair, for culturing keratinocytes from hair, and for generating induced pluripotent stem cells from keratinocytes.

13 Claims, 4 Drawing Sheets

(56) References Cited

U.S. PATENT DOCUMENTS

| | | | |
|---|---|---|---|
| 5,994,149 A | 11/1999 | Robinson et al. | |
| 6,607,699 B1 | 8/2003 | Elliott et al. | |
| 8,475,394 B1 | 7/2013 | Stivers | |

FOREIGN PATENT DOCUMENTS

| | | | | |
|---|---|---|---|---|
| JP | 2003052452 A | * | 2/2003 | |
| JP | 3110766 U | * | 6/2005 | |
| WO | WO 2001/18239 A1 | | 3/2001 | |

OTHER PUBLICATIONS

Aasen et al., "Efficient and rapid generation of induced pluripotent stem cells from human keratinocytes," Nat Biotechnol. Nov. 2008;26(11):1276-84. doi: 10.1038/nbt.1503. Epub Oct. 17, 2008.
International Search Report and Written Opinion for International Application No. PCT/EP2017/075336, dated Dec. 21, 2017 (13 pages).

* cited by examiner

SYSTEM FOR THE ASSERVATION OF HAIR SAMPLES

CROSS REFERENCE TO RELATED APPLICATION

This application is a continuation of international patent application PCT/EP2017/075336, filed on Oct. 5, 2017, designating the U.S., which international patent application claims priority from German patent application DE 10 2016 118 968.5, filed on Oct. 6, 2016. The entire contents of these priority applications are incorporated herein by reference.

BACKGROUND

The invention concerns a system for asservation of hair samples, which have a hair root and a hair shaft.

The safe asservation of hair samples, for example by storage or during transport, is of enormous importance in many areas of science and medicine. Intact hair samples are used for a variety of analyses, but also for cell cultivation.

Since hair samples—without a professional asservation—are quickly damaged after sampling under exposure to air, the asservation of hair samples is faced with a multitude of challenges.

In order to be able to use a hair sample in a further application, it is absolutely necessary that the sample remains completely intact. This means that above all the hair root with the outer hair root sheath must be undamaged, as this often serves as the basis for a further application/use. Furthermore, the hair sample must not dry out. This also prevents possible further application.

Before a possible further application of the hair sample, the sample is taken. Here hair is taken from a test person. Hair removal is usually carried out by trained personnel who are able to remove the hair together with the hair roots by trained hand movements and prepare them for further application.

Often there is a certain period of time between the hair removal and the further use of the hair sample, so that the hair has to be preserved in the meantime. In some cases, the hair sample is not taken at the same location as the planned further application, so that the hair sample must be safely preserved during its transport to an appropriate laboratory. According to the current state of the art, this transport is extremely difficult and sometimes very time-consuming.

Some of the challenges that arise during asservation are ensuring a functioning hair root, preferably with an outer hair root sheath, over time, and ensuring that the hair does not dry out. If the hair root breaks down or dries out during transport, the hair sample is irretrievably destroyed for further application/use and can no longer be used.

Currently, hair samples are transported in media containers, for example 15 or 50 mL round bottom tubes, in a liquid medium. This often leads to contamination of the hair sample, as the design and handling of the storage container cannot guarantee sterility over a longer period of time.

In addition, due to the liquid state of aggregation of the medium, it cannot be ensured during the entire transport that the hair will be wetted by the liquid over the entire time. This may occur if the sample container is shaken heavily during transport; however, this is often unavoidable. For example, the hair sample can attach itself to the lid of the transport container so that it is no longer wetted with the medium during further transport and dries out.

More often, however, the medium leaks out of the container, as the container is not tightly sealed for solvents due to the screw cap. The separation of the sample from the medium as well as the leakage of the medium leads to a drying out of the hair sample which is irretrievably destroyed for further treatment.

The use of liquid media also has the disadvantage that customs problems arise when transporting liquids in particular. Furthermore, in some countries it is already not permitted to ship liquids, so that no hair sample can be sent to or from these countries by post.

The transport and storage of hair samples are usually carried out at low, constant temperatures, so that the hair sample container must be cooled continuously during the entire period.

Transport at constant temperatures sometimes requires constant cooling, which, depending on the transport route or the duration of the transport, can only be carried out with very high technical effort or not at all. Alternatively, hair samples can be transported at room temperature, provided the transport only takes a few days.

According to the current state of the art, a secure asservation is extremely laborious and costly.

Also against the background of new findings on the derivation of stem cells from hair samples, there is a great need for a safe and sterile transport/storage of hair samples. Accordingly, Aasen et al. (T. Aasen et al. nature biotechnology, 26, 2008, 1276-1284) describe that the generation of induced pluripotent stem cells (iPS) from keratinocytes of hair roots, following cell cultivation, is possible.

In order to obtain iPS, the hair sample is transferred to an appropriate target laboratory after hair removal. The sample is then further processed in an elaborate process which includes the steps of hair plating, keratinocyte culturing and reprogramming. This procedure can take up to 35 days and can currently only be carried out by a qualified specialist.

This new possibility of further applications/uses of a hair sample makes the safe asservation of hair samples an increasingly important tool for scientific and medical research.

Against this background, it is the object of the present invention to provide a new system for the asservation of a hair having a hair root and a hair shaft, by means of which the disadvantages of the systems known in the state of the art described above can be overcome.

SUMMARY

According to the invention, this object is solved by a system for asservation of at least one hair having a hair root and a hair shaft, the system comprising: a hair receiving/accommodating device comprising a carrier plate element/member for depositing the hair and a cover plate element/member to be placed onto the carrier plate element for partially covering the hair, characterized in that the carrier plate element has a first end, a second end, an outer surface and a hair receiving surface, the hair receiving surface having a first portion extending from the first end to a central region of the hair receiving surface, and a second portion extending from the central region to the second end, the first portion having a structure having recesses and/or depressions for receiving the hair root, and a second portion for receiving the hair shaft, and in that the cover plate element for covering and/or pinching the hair on the carrier plate element is designed and dimensioned such, that only the second portion of the hair receiving surface of the carrier plate element is covered.

According to the invention, the object is also solved by using the system to cultivate keratinocytes and/or transport and/or store a hair comprising a hair root and hair shaft.

With the system according to the invention, the safe asservation of hair with a hair root and a hair shaft is possible over a longer period of time at room temperature. The individual hairs are covered and/or clamped between a carrier plate element and a cover plate element. This defines and fixes the hair. With the system according to the invention, a shifting/slippage of the hair is avoided with the inventive system, since the cover plate element pinches at least a part of the hair shaft. The hair root, preferably with an outer hair root sheath, lies securely on the carrier plate element.

According to the invention, shifting of the hair sample can already be prevented by prior moistening of the hair or by polar/electrostatic surface treatment. A moistened hair or a charged hair can already stick to the hair receiving surface by itself.

According to the invention, the term "hair shaft" refers to the area of the hair that protrudes from the skin and is visible to the naked eye. The section in the skin is understood as "hair root" according to the invention. The hair root comprises the outer hair root sheath with its hair keratinocytes capable of dividing.

According to the invention, "asservation" refers to the covering, clamping/pinching and storing of hair samples, whereby asservation is also possible during transport.

Presently, "hair sample" means a sample of at least one hair which has both a hair shaft and a hair root. The "hair sample" according to the invention is preferably retrieved from a subject who is preferably a mammal, preferably a human, so that different hair samples differ in the respective donor.

According to the invention, the hair-receiving surface of the carrier plate element has at least two portions which may differ in surface structure; a first portion and a second portion which adjoin each other in a central region and which each occupy half of the surface according to an embodiment. It is understood that this 50-50 division is exemplary only, and the division into the first and second sections may also be otherwise percentage divided, from between 10% of the hair-receiving surface of the carrier plate element for the first section and 90% for the second section, to approximately 90% for the first section and 10% for the second section. Preferred area distributions for the area ratio of the first section to the second section are approx. 30:70, approx. 40:60; approx. 50:50, approx. 60:40, approx. 30:70, whereby it is understood that these area specifications do not have to be absolutely exact.

According to another embodiment, the first section occupies one third and the second occupies two thirds of the area, or vice versa, so that the first section occupies two thirds of the area and the second section one third. The same applies to the division of the area into quarters, fifths etc.

While the first section has a structure having recesses and/or depressions, the second section preferably has a smooth surface. The smooth surface of the second section allows better covering and/or pinching of the hair through the cover plate element than, for example, on the first section. Depending on the embodiment, the middle section may have a structure with recesses and/or recesses and/or alternatively a smooth surface. Other surface structures of the middle area and the second section are possible according to the invention.

According to a preferred embodiment, the carrier plate element has an elongated shape. According to a further embodiment, preferred dimensions for the length are approx. 50 to 150 mm, in particular approx. 65 to 85 mm, for the width approx. 15 to 45 mm, in particular 20 to 30 mm, and for the height approx. <2.5 mm, in particular <1 mm. In a preferred embodiment, the carrier plate element, for example, has the dimensions 76 mm (length), 26 mm (width) and 1 mm (height). Accordingly, according to a preferred embodiment, the cover plate element is essentially oblong or square. According to a further embodiment, preferred dimensions for the length are approx. 25 to 75 mm, in particular approx. 35 to 40 mm, for the width approx. 15 to 45 mm, in particular 20 to 30 mm, and for the height <3 mm, in particular <1 mm. Thus, the carrier plate element and the cover plate element are essentially rectangular, preferably with two narrower/shorter sides and two longer sides. According to the invention, the carrier plate element as well as the cover plate element can have other shapes such as oval, round or curved shapes.

According to a preferred embodiment of the system according to the invention, the cover plate element is fastened/attached to the carrier plate element by means of a fastening means for covering and/or clamping of at least one hair comprising a hair root and a hair shaft.

"Fastening means" is understood to encompass any means by which the two plate elements can be fastened, whereby it is preferred if the fastening means can be applied/placed reversibly so that the hair sample can be rearranged and clamped again if necessary. A possible fastening means is, for example, a clamp (e.g. clip system) which encloses the carrier plate element and the cover plate element. Alternatively, and also according to the invention, the two plates can be glued together, so that the hair is trapped in the hair receiving device. Furthermore, the two plate elements can also be clamped together due to their construction, for example by sliding them together or inserting them into each other. It is also possible to screw the plates together.

This embodiment has the advantage that a better fixation of the hair shaft within the hair receiving device is achieved by the cover plate element. A shifting of the plates, as well as the hair sample, can be prevented by this embodiment.

In another form of the invention, the first end of the carrier plate element is elevated compared to the rest of the carrier plate element.

"Elevated" means that the first end has a greater height compared to the second end of the carrier plate element. According to the invention, the elevation can occur in steps, so that a preferably narrow band rests on the carrier plate element at the first end. Similarly, the elevation can be linear, in accordance with the invention, so that the first portion in the range to the first end continuously increases in height. This linearly increasing elevation can extend over the entire first portion, or only towards the first end.

This embodiment has the advantage that a shifting of the hair root, which is placed onto the first section of the hair receiving surface, beyond the first end can be prevented. In addition, the elevation of the carrier plate element protects the hair root from external influences, starting from the first end of the carrier plate element.

According to a preferred embodiment of the invention, the structure comprising the depressions and/or recesses of the first portion of the carrier plate element between the hair-receiving surface and the outer surface is wholly permeable.

This embodiment has the advantage that the hair root, which is located on the first section of the hair receiving surface, is accessible from all sides and at the same time is fixed via its hair shaft on the hair receiving surface.

According to a further preferred embodiment, the system further comprises a transport container and/or a storage container with at least one opening for insertion of at least one hair receiving device, wherein the opening of the transport container and the storage container has substantially the same height and width corresponding to the first end of the hair receiving surface, such, that the hair receiving device, with its first portion, is at least partially insertable into the opening of the transport container.

This embodiment has the advantage that the asservation of hair samples can be carried out within a transport or storage container. In particular, the hair root can be protected from external influences. In addition, this embodiment allows sterile transport or storage of hair samples.

According to a preferred embodiment, the transport or storage container has an elongated shape. Preferably, the hair receiving device—via one of its narrow/shorter sides—is inserted/pushed into the transport or storage container. Thus, the opening, in another embodiment, corresponds to the preferred dimensions for the length of approx. 16 to 46 mm, in particular approx. 21 to 31 mm, for the height approx. <4 mm, in particular <2 mm.

The dimensions of the transport container essentially correspond to the dimensions of the carrier plate element, so that space-saving transport of hair samples can be achieved. According to a further embodiment, preferred dimensions for the length are approx. 40 to 100 mm, in particular approx. 50 to 70 mm, for the width approx. 25 to 70 mm, in particular approx. 35 to 45 mm, and for the height approx. 10 to 40 mm, in particular 15 to 30 mm.

In a preferred embodiment, the storage container has several openings to accommodate carrier plate elements. It is therefore possible to store several carrier plate elements in parallel. This enables a space-saving storage. It will be clear to the expert, which dimensions of the storage container are particularly advantageous. In addition, he will be able to determine the number of openings for the carrier plate elements in the storage container that will be appropriate.

In another embodiment of the system, the transport container comprises moisturizing gels.

According to the invention, a "gel" is a finely dispersed system, analogous to a viscoelastic fluid. The fluid properties of the gel according to the invention lie between those of an ideal liquid and those of an ideal solid.

This embodiment has the advantage that moisturizing gels can prevent the hair root and the hair shaft from drying out. Due to the construction of the transport container and the hair receiving device placeable inside, as it is designed according to the invention, the hair root can always be wetted with the moisturizing gel, which is preferably located on the outer surface, without drowning in the gel. Thus, the hair root is wetted on the one hand with the moisturizing gel, on the other hand, however, stored in air.

Due to the consistency of the gel, this embodiment allows the gel to remain safely in the transport container. Leakage, such as with liquids, is avoided.

According to the invention, the transport or storage container may have at least approximately the same dimensions as the hair receiving device. This results in the advantage of a particularly space-saving asservation of hair.

According to the invention, the transport or storage container may have several openings for several hair receiving devices. This makes it possible to transport and store several hair samples in a single container. Material as well as storage and transport costs can be saved.

If the storage takes place under cooling, this embodiment has the advantage that costs caused by the cooling are kept low, since several hair receiving devices can be stored next to each other as well as one behind the other in the storage container. This results in a particularly space-saving storage of hair samples.

In accordance with a preferred embodiment of the system according to the invention, the system further comprises a cultivation container having at least one first opening for insertion of at least one hair receiving device, the first opening of the cultivation container having substantially the same height and width corresponding to the first end of the hair receiving surface, in that the first section of the hair receiving device can be inserted at least partially into the opening of the cultivation container, and also a second opening for exchanging and/or adding cultivation media.

This embodiment has the advantage that keratinocytes can be cultivated from at least one hair root. The keratinocytes obtained can be used for genetic analysis like any other proliferating cell type.

Due to the simple handling, the system according to the invention can be used by any person without prior training to cultivate keratinocytes.

In a further embodiment, the system can be used to generate induced pluripotent stem cells (iPS). The generation of induced pluripotent stem cells is based on the keratinocytes, which are cultivated from the hair roots. With this embodiment, both, cultivation and reprogramming, can be carried out within a container without replating.

According to this embodiment, the process of iPS generation from hair keratinocytes can be simplified, in a reproducible and cost-effective way for established laboratories.

The system according to the invention also offers the possibility of removing individualized cells on a large scale at low cost and preserving them as a biobank without the need for direct reprogramming. In the course of this, a completely automated barcode system can be introduced that guarantees anonymous sample collection and can meet data protection requirements.

According to the invention, the cultivation container has at least one opening for inserting a hair receiving device. According to the invention, the cultivation container can also have several openings for inserting several hair receiving devices. This makes it possible to cultivate different hair samples on different hair receiving devices in parallel in one cultivation container. This embodiment has the advantage of saving time and money.

In a preferred embodiment, the cultivation container has a cuboid shape. In another embodiment, the shape of the cultivation container corresponds to a cultivation flask shape, for example a T25 cell culture flask. The cultivation container also preferably has a lateral opening for the hair receiving device, which has the preferred dimensions corresponding to the length of approx. 16 to 46 mm, in particular approx. 21 to 21 mm and corresponding to the height of approx. <4 mm, in particular <2 mm.

In a preferred embodiment, the second opening, for the exchange and/or addition of culture media, corresponds to a bottle opening, a screw cap or a lid.

The cultivation container may also have several openings for the exchange and/or addition of culture media. This allows the cultivation of keratinocytes and/or the reprogramming to iPS cells to be automated, resulting in time and cost savings.

According to the invention, the hair receiving device and the culture container can be made of any material that allows sufficient adherence of the cells to the culture surface.

According to the invention, the cultivation surface can represent the hair receiving surface as well as the outer surface of the carrier plate element.

According to another embodiment, the carrier plate element, cover plate element, transport container, cultivation container and/or storage container are made of a material selected from the group consisting of polypropylene, polyethylene, polysulfone, Teflon™ (polytetrafluoroethylene), fluorinated ethylene propylene (FEP), Teflon™ PFA (perfluoroalkoxy alkane), polystyrene, polycarbonate, styrene, acrylonitrile, acrylic, glass and mixtures thereof.

This embodiment has the advantage that the materials are chemically inert. These materials are stable towards various solvents, so that the dissolving of substances from the material is at least largely impossible.

Some of these materials have the advantage of having electrostatic properties. Due to these properties, it is possible that the hair is mainly fixed by the electrostatic attraction on the hair receiving surface. A shifting of the hair, especially the hair root, can thus be prevented at least partially.

In a further embodiment, the cultivation container comprises cultivation media selected from the group consisting of compounds for improving cell adhesion, nutrient media, keratinocyte media, fibroblast growth factors, peptidases, antibiotics, antifungals or mixtures thereof.

This form of cultivation has the advantage that—due to the presence of the cultivation medium—the keratinocytes can be cultivated from the hair root. This embodiment has the advantage that keratinocytes can also be cultivated by untrained personnel.

The invention thus concerns a system for the asserversion of hair, which has at least the hair receiving device according to the invention and, if applicable, the transport or storage container according to the invention and, if appropriate, the cultivation container, whether additional or alternative. This provides a practical modular system that significantly simplifies both the handling and cultivation of the hair cells.

Further advantages result from the figures and from the following description of preferred embodiments.

It goes without saying that the features mentioned above and those still to be explained below can be used not only in the respective combination indicated, but also in other combinations or in a unique position, without leaving the scope of the present invention.

BRIEF DESCRIPTION OF THE DRAWINGS

Embodiments of the invention are shown in the figures and are explained below. They show.

DESCRIPTION OF PREFERRED EMBODIMENTS

Function-equivalent elements are denoted with the same reference signs in all figures, even in different embodiments.

Figure 1A:
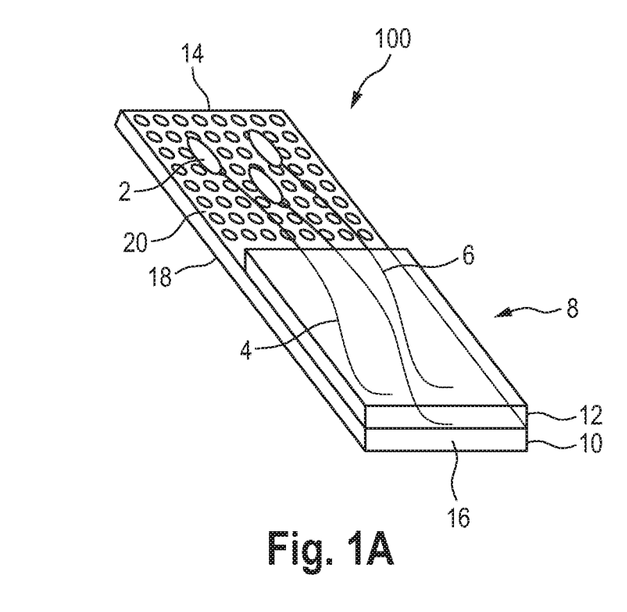
FIG. 1A shows a schematic representation of a first embodiment of the system for the asserversion of at least one hair having a hair root and a hair shaft.

FIG. 1A shows a schematic representation of a first embodiment of a system 100 for the asserversion of at least one hair 6 having a hair root 2 and a hair shaft 4. A hair receiving device 8, which is constructed from a carrier plate element 10 and a cover plate element 12, can be seen. The hair receiving device 8 is designed such that a hair 6, which has a hair root 2 and a hair shaft 4, is covered between the carrier plate element 10 and the cover plate element 12. A large part of the hair shaft 4 is covered, with the rest of the hair shaft 4 and the hair root 2 resting on the hair receiving surface 20 of the carrier plate element 10.

In addition to the rectangular shape shown for the hair receiving device 8, any other shape is possible, such as rectangular, oval or round. Depending on the design, it can be advantageous that the hair receiving device is 8 T-shaped.

As shown in FIG. 1A, the carrier plate element 10 has a first end 14 and a second end 16. In addition to the outer surface 18, which forms the lower surface in this figure, the carrier plate element 10 also has a hair receiving surface 20. This hair receiving surface 20 has a first section that extends from the first end of 14 to a central area of the hair receiving surface 20. This first section has a structure with recesses and/or depressions to accommodate the hair root 2. The second section extends from the central area to the second end 16, which has a smooth surface. The smooth surface is particularly advantageous for covering the hair with the cover plate element 12.

In a preferred embodiment, the system 100 is used for asserversion of hair 6 for single use. The system 100 can be sterile packed before use.

Figure 1B:
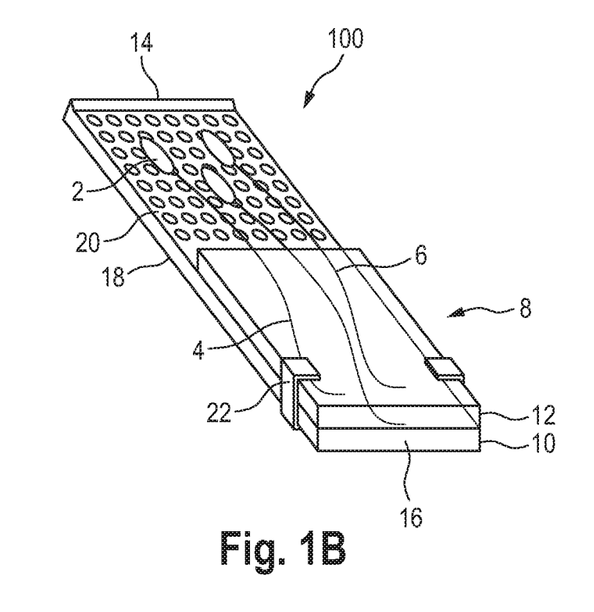
FIG. 1B shows a schematic representation of a second embodiment of the system for the asserversion of at least one hair having a hair root and a hair shaft.

FIG. 1B shows a second embodiment of the system 100 for asserversion of at least one hair 6 comprising a hair root 2 and a hair shaft 4. This schematic representation contains the schematic representation from FIG. 1A with the features described therein.

In FIG. 1B the cover plate element 12 is fastened to the carrier plate element 10 via a fastening element 22. With the fastening element 22, a displacement/shifting of the hair 6 with the hair shaft 4 in the second portion can be largely prevented. Furthermore, according to the invention, any form of fastening means 22 is feasible which holds the carrier plate element 10 and cover plate element 12 together. For example, the plates can be glued, screwed or clamped.

Furthermore, the hair receiving device 8 and its carrier plate element 10 have an elevation at the first end 14. Elevation means that a cross-section of the first end of the first section preferably corresponds to the dimensions corresponding to the height of <5 to <1.5 mm, in particular <2 to 1.5 mm. A cross-section of the first and second ends of the hair receiving device therefore differ in height but not in width and length. The increase may be gradual or linear.

Figure 2:
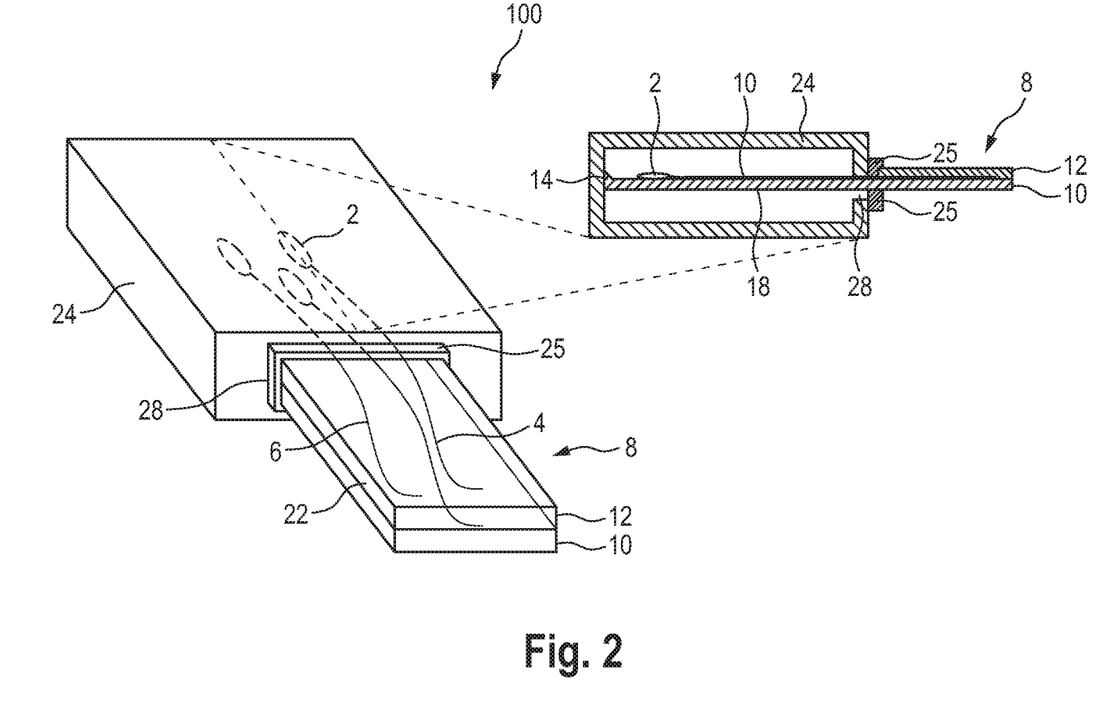
FIG. 2 shows a schematic representation of a third embodiment of the system for the asserversion of at least one hair having a hair root and a hair shaft, a transport container being shown next to the hair receiving device.

FIG. 2 shows a further embodiment of system 100 for asserversion of at least one hair 6 having a hair root 2 and a hair shaft 4, wherein a transport container 24 is shown next to the hair receiving device 8. In addition to the perspective view of the system 100, a cross-section of the system 100 can also be seen in this figure. The schematic representation of FIG. 2 also contains the schematic representation of the hair receiving device 8 from FIG. 1A with the features described there.

FIG. 2 also shows the hair receiving device 8, which is pushed/inserted through the opening 28 of the transport container 24 and is, thus, partly contained in the transport container 24. The opening 28 is such that it has substantially the same height and width corresponding to the first end 14 of the hair receiving surface 20, so that the hair receiving device 8 with its first section can be at least partially inserted into the opening 28 of the transport container 24. The partially exposed hair, which is not covered by the cover plate element 12, is thus stored in the transport container 24.

The transport container 24 preferably contains a moisturizing gel (not shown). This moisturizing gel has the advantage that drying out of hair 6 together with the hair root 2 and the hair shaft 4 can be prevented during transport. In addition to the moisturizing gel, there may be other moisturizing materials and/or liquids that can prevent hair from drying out. An advantage of the moisturizing gel is that due to the composition of the gel, the transport of hair 6 can also take place at room temperature. Furthermore, the disadvantages resulting from the transport with liquids are overcome due to the consistency of the gel.

The opening 28 of the transport container 24 may also have a seal 25. This seal 25 can prevent the hair from drying out and the gels in it from leaking out. According to the invention, any form of seal can be used as seal 25. For example, a seal type can be used to allow clipping of the hair receiving surface. This can create a tensile connection between the transport container and the hair receiving surface, which can be released by a release mechanism, e.g. by pressing sideways.

As shown in FIG. 2, the transport container 24 has approximately the same dimensions as the hair receiving device. This has the advantage that the transport container 24 together with the hair receiving device 8 is relatively small, which makes transport easier.

In the cross-section of the system 100, FIG. 2 further shows that the opening 28 for inserting the hair receiving device 8 is mounted within the transport container 24, such, that, when the hair receiving device 8 is in the transport container 24, both on the side of the hair receiving surface 20 and on the side of the outer surface 18 of the carrier plate element 10, two regions result within the transport container 24. An upper area is formed as well as a lower area, which is interrupted by the hair receiving device 8.

In one embodiment, the moisturizing gel may be in the upper area, while air circulation is possible in the lower area. The moisturizing gel may also be stored in the lower area of the transport container 24 so that air circulation can take place in the upper area.

FIG. 2 shows that the hair receiving device 8 is inserted into the transport container 24 with the hair receiving surface 20 facing upwards. It is also possible to push the hair receiving device 8 upside down into the transport container 24.

In FIG. 2 the transport container 24 has an opening 28 for the hair receiving device 8. In a preferred embodiment (not shown) the transport container 24 has several openings 28 for transporting several hair receiving devices 8. These hair receiving devices 8 can be arranged side by side or one behind the other. This means that the transport of several hair receiving devices 8 is particularly space-saving and cost-effective.

In a further embodiment (not shown), the first portion of the carrier plate element 10, which has a structure comprising recesses and/or depressions, is entirely permeable between the hair-receiving surface 20 and the outer surface 18. This embodiment has the advantage that if there is a moisturizing gel in the transport container 24, the hair root 2 can be partially wetted by the gel and the hair 6 can breathe in the air.

With the system 100, which has a hair receiving device 8 as well as a transport container 24, every individual—taking into account written and visual instructions—can independently remove hair from him-/herself or another person and prepare it for transport with simple hand movements. Furthermore, personnel trained for hair removal is no longer mandatory. The hair is pulled out with tweezers or by plucking the hair with the hand. Afterwards, the hair is simply placed and positioned on the carrier plate element 10 and the hair 6 is attached by the cover plate element 12. Finally, the hair can be transported by post at room temperature.

Figure 3:
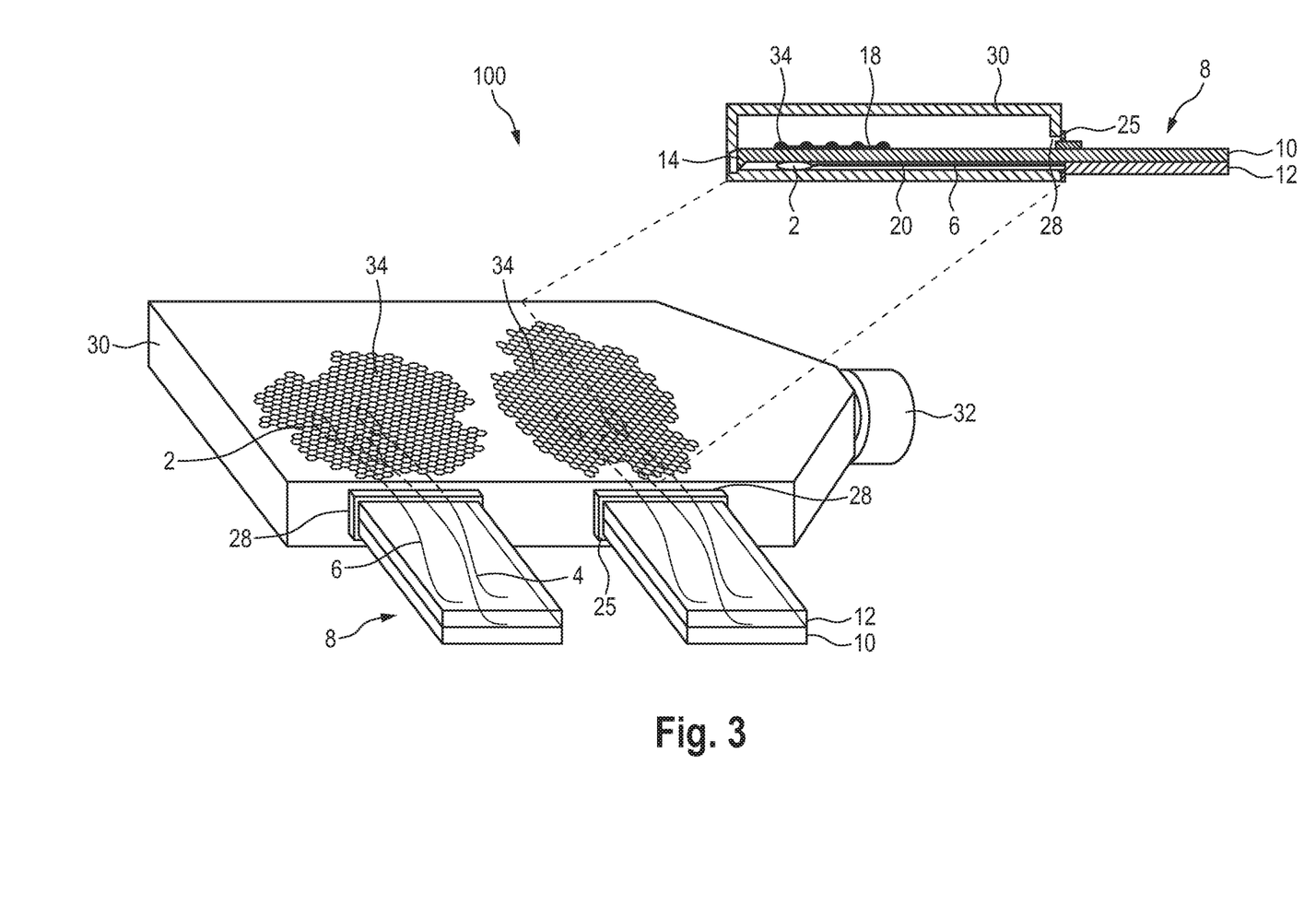
FIG. 3 shows a schematic representation of a fourth embodiment of the system for asserversion of at least one hair having a hair root and a hair shaft, wherein a cultivation container is shown next to the hair receiving device.
Figure 4:
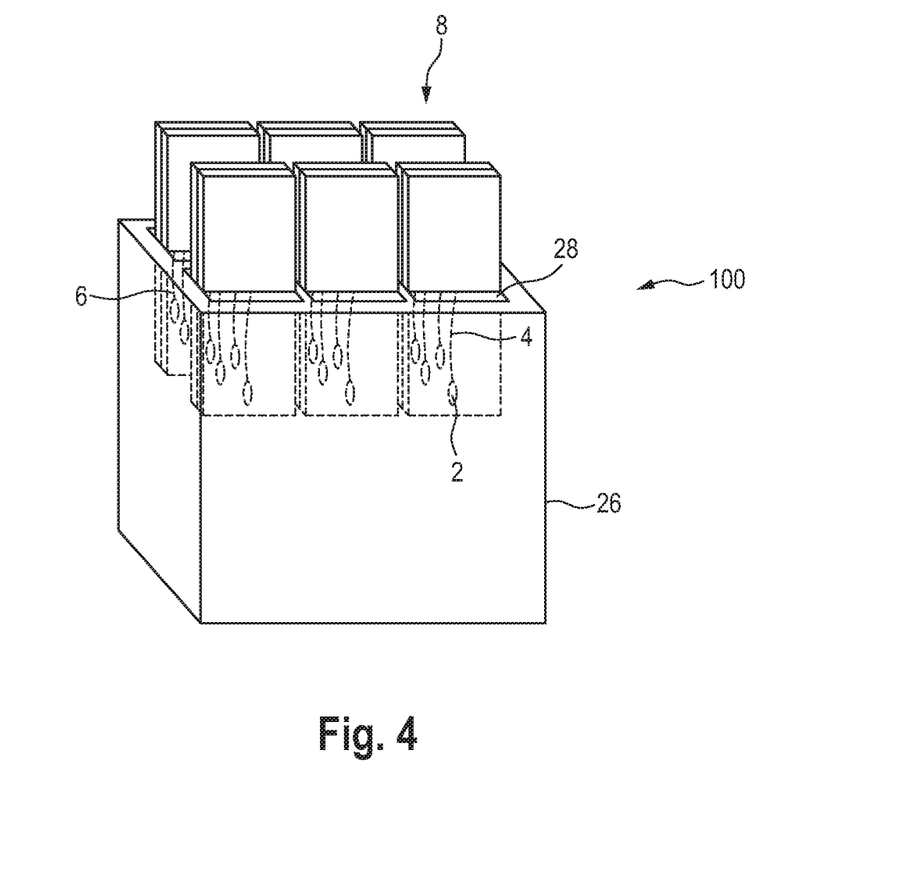
FIG. 4 shows a schematic representation of a fifth embodiment of the system for the asserversion of at least one hair having a hair root and a hair shaft, a storage container being shown next to the hair receiving device.

The hair receiving device 8 can be cultivated after transport in transport container 24 or after hair removal in a cultivation container 30 (see FIG. 3) or frozen in a storage container 26 (FIG. 4).

FIG. 3 shows a further embodiment of the system 100 for asservation of at least one hair 6 having a hair root 2 and a hair shaft 4, wherein in addition to the hair receiving devices 8 a cultivation container 30 is shown. In addition to the perspective view of System 100, a cross-section of System 100 can also be seen in this figure. The schematic diagram of FIG. 3 also contains the schematic diagram of the hair receiving device 8 from FIG. 1A with the features described there.

The hair receiving device 8 is partly located within the cultivating container 30. In addition to the first opening 28 for the insertion of a hair receiving device 8, the cultivation container 30 has a second opening 32 suitable for the exchange and/or addition of cultivation media.

FIG. 3 shows the second opening 32 as a screw cap. Another embodiment of opening 32 is possible. Furthermore, the cultivation container 30 can have several openings 32 for the exchange and/or addition of cultivation media (not shown). The cultivation of keratinocytes 34 in a continuous flow is possible by having several openings 32. This has the advantage that cultivation can take place automatically.

In addition to the cultivation of keratinocytes 34, it is also possible to re-program them into iPS cells in the cultivation container. If the cultivation container 30 has several openings 32 for the exchange and/or addition of cultivation media, a completely automated generation of iPS cells is also possible.

As the cross-section of the embodiment shown in FIG. 3 shows, the hair receiving device 8 is aligned such that the hair receiving surface 20 faces the bottom of the cultivation container 30 and the outer surface 18 of the carrier plate element 10 faces the top of the cultivation container 30. It is also shown that the opening 28 for the hair receiving device 8 is relatively close to the bottom of the cultivation container 30. In this embodiment the hair 6 lies with its hair root 2 on the inner bottom of the cultivation container 30. If the first portion of the carrier plate element 10 between the hair receiving surface 20 and the outer surface 18 is completely permeable, cell cultivation of the keratinocytes 34 can take place on the outer surface 18 of the carrier plate element 10.

In this embodiment, the distance between the hair receiving device 8, in particular the hair receiving surface 20, and the bottom of the culture container 30 is defined by the elevation of the first end 14. In another preferred embodiment, the bottom of the cultivation container 30 may have a recess so that the elevation of the first end 14 can be inserted into the recess (not shown). This results in a defined distance that can facilitate cell cultivation.

As already shown in FIG. 2, the opening 28 for the hair receiving device 8 of the cultivation container 30 has a seal 25. This seal 25 can prevent the leakage of liquids from the cultivation container 30. In addition to the seal 25, the opening 28 of the cultivation container 30 can have any form of seal that can prevent the culture medium or other liquids from leaking.

In another embodiment (not shown), opening 28 can also be closed by a closure, e.g. a rubber element or plastic lid. This has the advantage that the hair receiving device can be removed after sufficient growth of the keratinocytes. This allows the container to be closed securely, so that leakage of the cultivation media can be prevented. The previously removed hair receiving device can then be frozen or reused in another cultivation container. The keratinocytes, on the other hand, can continue to proliferate until confluence.

In FIG. 3 the cultivation container 30 has two hair receiving devices 8. It is also possible for the cultivation container 30 to have one or more hair receiving devices 8. These hair receiving devices 8 can be inserted next to each other or one above the other, whereby a juxtaposed row is preferred.

In the cultivation container 30 in FIG. 3, which has several openings 28 for hair receiving devices 8, several hair samples can be cultivated simultaneously. On the one hand, this can reduce the time required for work and material costs.

FIG. 4 shows a further embodiment of system 100 for asservation of at least one hair 6 having a hair root 2 and a hair shaft 4, wherein a storage container 26 is shown next to the hair receiving device 8. The schematic representation of FIG. 4 also contains the schematic representation of the hair receiving device 8 from FIG. 1A with the features described there.

FIG. 4 shows that several hair receiving devices 8 can be arranged next to each other as well as behind each other. This enables a compact storage of hair samples.

FIG. 4 also shows that the openings 28 of the hair receiving device 8 are arranged both side by side and one behind the other. According to another embodiment, a different arrangement of the openings 28 can be provided. The openings are preferably arranged in such a way that as many hair receiving devices as possible can be stowed in a storage container 26.

In FIG. 4, the hair receiving devices 8 are inserted into the storage container 26 from above. In other embodiment (not shown), the hair receiving devices 8 can also be pushed or inserted into the storage container 26 from the other sides. In addition, the storage container according to the invention can also comprise only one opening for a hair receiving device 8 (similar to the transport container 24).

The storage of hair 6 preferably takes place at low temperatures, so that the hair samples can be frozen. For this purpose, the storage container 26 can be filled with a refrigerant such as isopropanol, which enables continuous freezing at approx. −90° C. Cooling is preferably achieved by means of liquid nitrogen. Furthermore, the storage container can be filled with a freezing medium; for example, 90% FBS, 10% DMSO. Storage in a freezer at −80--90° C. is, thus, possible.

If storage is carried out at low temperatures, the storage container is preferably made of freeze-resistant materials. In addition, the storage container may have a means of permitting continuous thawing of the sample.

In addition to storing hair 6, keratinocyte cultures can also be stored if they have been cultivated beforehand.

The containers in FIGS. 2 to 4 are preferably sterile, so that further applications of the hair 6 can take place without restrictions.

What is claimed is:

1. System for the asservation of at least one hair having a hair root and a hair shaft, the system comprising:
   a hair receiving device comprising a carrier plate element for having the hair deposited thereon and a cover plate element to be placed onto the carrier plate element for partially covering the hair, wherein
   the carrier plate element has a first end, a second end, an outer surface and a hair-receiving surface, the hair-receiving surface having a first portion extending from the first end to a central region of the hair-receiving surface, and a second portion extending from the central region to the second end, the first portion having a structure having recesses and/or depressions for receiving the hair root, and the second portion for receiving the hair shaft, wherein the structure having recesses and/or depressions is completely permeable between the hair-receiving surface and the outer surface, and wherein
   the cover plate element is designed and dimensioned for covering and/or pinching the hair on the carrier plate element, such, that only the second portion of the hair-receiving surface of the carrier plate element is covered by the cover plate element.

2. The system according to claim 1, wherein the cover plate element is attachable to the carrier plate element by means of a fastening means for covering and/or clamping the at least one hair comprising the hair root and the hair shaft.

3. The system according to claim 1, wherein the first end of the carrier plate element is elevated in relation to the remaining of the carrier plate element.

4. The system according to claim 1, further comprising a transport container and/or a storage container with at least one opening for inserting at least one of the hair receiving device, wherein the opening of the transport container and/or the storage container has substantially the same height and width corresponding to the first end of the hair receiving surface, such, that the hair receiving device, with its first portion, is at least partially insertable into the opening of the transport container.

5. The system according to claim 1, further comprising a cultivation container having at least one first opening for insertion of at least one hair receiving device, the first opening of the cultivation container having substantially the same height and width corresponding to the first end of the hair receiving surface, such, that the hair receiving device, with its first portion, is at least partially insertable into the first opening of the cultivation container; and the cultivation container has a second opening for exchanging and/or adding cultivation media.

6. The system according to claim 1 wherein the carrier plate element and/or the cover plate element are made of a material selected from the group consisting of polypropylene, polyethylene, polysulfone, polytetrafluoroethylene, fluorinated ethylene propylene (FEP), perfluoroalkoxy alkane, polystyrene, polycarbonate, styrene, acrylonitrile, acrylic, glass and mixtures thereof.

7. The system according to claim 5, wherein the cultivation container comprises cultivation media selected from the group consisting of compounds for improving cell adhesion (coating substrates), nutrient media, keratinocyte media, fibroblast growth factors, peptidases, antibiotics, antifungals or mixtures thereof.

8. The system according to claim 1, wherein the transport container comprises moisturizing gels.

9. A method for transporting and/or storing of hair, the method comprising the steps of
providing a hair comprising a hair root and a hair shaft,
placing the hair in the system of claim 1,
thereby storing and/or transporting the hair.

10. A method for culturing keratinocytes from a hair, the method comprising the steps of
providing a hair comprising a hair root and a hair shaft,
placing the hair in the system of claim 1,
adding keratinocytes cultivation medium to the system, and
incubating the hair for a period of time,
thereby culturing keratinocytes from the hair.

11. A method for generating induced pluripotent stem cells from keratinocytes, the method comprising the steps of
providing a hair comprising a hair root and a hair shaft,
placing the hair in the system of claim 1,
adding keratinocytes cultivation medium to the system,
incubating the hair for a period of time,
inducing pluripotent stem cells,
thereby generating induced pluripotent stem cells.

12. The system according to claim 4, wherein the transport container and/or the storage container is made of a material selected from the group consisting of polypropylene, polyethylene, polysulfone, polytetrafluoroethylene, fluorinated ethylene propylene (FEP), perfluoroalkoxy alkane, polystyrene, polycarbonate, styrene, acrylonitrile, acrylic, glass and mixtures thereof.

13. The system according to claim 5, wherein the cultivation container is made of a material selected from the group consisting of polypropylene, polyethylene, polysulfone, polytetrafluoroethylene, fluorinated ethylene propylene (FEP), perfluoroalkoxy alkane, polystyrene, polycarbonate, styrene, acrylonitrile, acrylic, glass and mixtures thereof.

* * * * *